United States Patent [19]

Boyer et al.

[11] Patent Number: 5,378,629
[45] Date of Patent: Jan. 3, 1995

[54] WASH COMPOSITION FOR DETERMINATION OF MICROORGANISMS ASSOCIATED WITH PERIODONTAL DISEASES

[75] Inventors: Bradley P. Boyer; Paul B. Contestable; Brian A. Snyder, all of Rochester, N.Y.

[73] Assignee: Eastman Kodak Company, Rochester, N.Y.

[21] Appl. No.: 72,029

[22] Filed: Jun. 7, 1993

Related U.S. Application Data

[62] Division of Ser. No. 774,019, Oct. 8, 1991, Pat. No. 5,248,595.

[51] Int. Cl.⁶ .......................................... G01N 33/569
[52] U.S. Cl. .................................... 436/17; 436/8; 436/518; 436/826; 435/962; 435/967
[58] Field of Search ................... 436/17, 18, 518, 826, 436/534, 8; 435/962, 967, 970

[56] References Cited

U.S. PATENT DOCUMENTS

| | | | |
|---|---|---|---|
| 4,299,916 | 11/1981 | Litman et al. | 435/6 |
| 4,617,383 | 10/1986 | Jaskowski | 536/2 |
| 4,652,529 | 3/1987 | Collins et al. | 436/92 |
| 4,720,455 | 1/1988 | Babu et al. | 435/7 |
| 4,965,191 | 10/1990 | Warren, III et al. | 435/7 |
| 4,981,786 | 1/1991 | Dafforn et al. | 435/7 |
| 5,017,474 | 5/1991 | McClune et al. | 435/7 |
| 5,124,245 | 6/1992 | Cummins et al. | 435/5 |
| 5,252,457 | 10/1993 | Snodgrass et al. | 435/5 |

FOREIGN PATENT DOCUMENTS 337785  4/1989  European Pat. Off. .
0328388  8/1989  European Pat. Off. .

OTHER PUBLICATIONS

Contestable et al. J. Dent. Res. 69 (Spec Issue March) (1990) 243 Abstract 1077.

*Primary Examiner*—James C. Housel
*Assistant Examiner*—Long V. Le
*Attorney, Agent, or Firm*—J. Lanny Tucker

[57] ABSTRACT

An aqueous wash composition has been found useful in methods for determination of specific binding ligands. The composition is buffered to a pH of less than or equal to 6 or greater than or equal to 9. It also includes as its essential component at least about 0.1 weight percent of an anionic surfactant which is represented by the formula:

$$[A\text{-}SO_{3+y}]^{-(1+y)}[X^{+m}]_n$$

wherein A is a hydrocarbon having a molecular weight of at least about 180, $X^{+m}$ is hydrogen or a monovalent or divalent cation, m is 1 or 2, is 0 or 1, and n is 1 or 2 provided that m and n are not both 2. Optionally and preferably, the wash composition also includes a nonimmunoreactive protein. This wash composition is particularly useful in methods for determination of microorganisms associated with periodontal diseases. Such methods can be of a variety of formats, but immunometric assays are particularly useful. The wash composition can be included as part of a diagnostic test kit.

8 Claims, 5 Drawing Sheets

WASH COMPOSITION FOR DETERMINATION OF MICROORGANISMS ASSOCIATED WITH PERIODONTAL DISEASES

This is a divisional of application Ser. No.774,019, filed Oct. 8, 1991, now U.S. Pat. No. 5,248,595.

FIELD OF THE INVENTION

The present invention relates to an aqueous wash composition, a diagnostic test kit and a method for using the wash composition to determine microorganisms associated with periodontal diseases. In particular, the method is useful for the determination of any of the microorganisms *Actinobacillus actinomycetemcomitans*, *Prevotella intermedia* (formerly known as *Bacteroides intermedius*) or *Prophyromonas gingivalis* (formerly known as *Bacteroides gingivalis*).

BACKGROUND OF THE INVENTION

There is a continuous need in medical practice, research and diagnostic procedures for rapid, accurate and qualitative or quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, dental plaque, gingival crevicular fluid and other biological specimens has to be determined in an accurate and rapid fashion for suitable diagnosis or treatment.

To provide such determinations, various methods have been devised for isolating and identifying biological substances employing specific binding reactions between the substance to be detected (sometimes identified as a "ligand") and a compound specifically reactive with that substance (sometimes identified as a "receptor").

After the formation of a specific binding complex between ligand and receptor, it is usually necessary to separate the complex from uncomplexed materials. A most common specific binding reaction involves an antigen (or antigen-like material) and its corresponding antibody which form an immunological complex. Uncomplexed antigen and antibodies are generally separated from the complex using various techniques. For example, separation may be accomplished by filtration, centrifugation or affinity chromatography. However, in most assays, the complex is solubilized and uncomplexed materials are washed from it. Common wash solutions include distilled water, various buffers and a number of solutions containing nonionic, anionic or cationic surfactants.

It has been found, however, that not every wash solution will effectively remove uncomplexed materials in every type of assay for a specific ligand. By effectiveness is meant that the uncomplexed materials are removed to such an extent that the assay result reflects only the presence of complexed materials with minimal background or cross-reactivity between the ligand and non-specific binding proteins. Thus, what may be useful as a wash composition for one assay is not necessarily useful in another. If the wash composition is ineffective, unwanted background may be present thereby obscuring the true assay result. One undesired result would be "false positives" from too high background or cross-reactivity. Another undesired result would be a true positive, but the background could obscure the magnitude of the positive result.

Specific microorganisms have been implicated as indicators for a number of periodontal diseases in humans and animals, such as gingivitis and periodontitis. The importance of such diseases is growing in the human population, especially as people live longer, and prevention of such diseases is becoming of considerable importance to dentists, insurance carriers and the health industry in general. In addition, proper dental care for animals is a growing concern in our culture.

Detection of microorganisms associated with periodontal diseases has been accomplished using culture techniques, DNA probes and a number of immunological procedures, such as agglutination assays, enzyme linked immunosorbent assays (ELISA) and others known in the art. ELISA utilizes the reaction of an extracted antigen from the microorganism(s) and the corresponding antibody to form an immunological complex. As noted above, usually uncomplexed materials are washed from the complex in order to provide an accurate assay result.

An advance in the art in the detection of microorganisms associated with periodontal diseases is described and claimed in the pending application U.S. Ser. No. 468,392 (filed Jan. 22, 1990 by Snyder). This case describes the simultaneous detection and differentiation of these microorganisms, and particularly *Actinobacillus actinomycetemcomitans*, *Porphyromonas gingivalis* and *Prevotella intermedia*, in an immunometric (also known as "sandwich") assay using water-insoluble reagents in defined regions of a microporous filtration membrane. During the assay, uncomplexed materials were washed through the membrane using a common wash solution of sodium decyl sulfate in water (pH 7).

While the noted simultaneous assay represents an important advance in the art for detecting the noted microorganisms, in some cases, false positives were observed when a specimen containing high levels of one or more of the three microorganisms was contacted with the different regions of the membrane substrate containing the antibody reagents. A solution to this problem is critical since it is highly important for the user of the assay to discriminate among the microorganisms for effective diagnosis and treatment of disease without significant apparent cross-reactivity between an antigen and non-specific antibodies.

SUMMARY OF THE INVENTION

The problem noted above was solved by using a very specific wash composition in the assay. This aqueous wash composition is buffered to a pH of less than or equal to about 6 or greater than or equal to about 9, and comprises at least about 0.1 weight percent of an anionic surfactant which is represented by the formula:

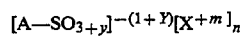

$$[A-SO_{3+y}]^{-(1+y)}[X^{+m}]_n$$

wherein A is a hydrocarbon having a molecular weight of at least about 180, $X^{+m}$ is hydrogen or a monovalent or divalent cation, m is 1 or 2, y is 0 or 1, and n is 1 or 2 provided that m and n are not both 2.

This invention also provides a diagnostic test kit useful for the determination of a specific binding ligand, comprising, in individual packaging:

(1) the aqueous wash composition described above, and (2) a receptor for a target specific binding ligand.

Moreover, a method for the determination of a microorganism associated with periodontal disease comprises the steps of:

A. forming a water-insoluble complex of an antigen extracted from a microorganism associated with periodontal disease with an antibody specific for the antigen, B. separating uncomplexed materials from the water-insoluble complex by washing with the aqueous wash composition described above, and C. detecting the water-insoluble complex as a determination of the microorganism.

The present invention resides in the use of a particular wash composition which has been shown to reduce or eliminate false positives in assays, particularly in assays for microorganisms associated with periodontal diseases. However, it is to be understood that the efficacy of the wash composition is not limited to the specific embodiments demonstrated herein, but it can be used in any type of specific binding assay whereby uncomplexed materials are removed from an insolubilized complex.

The wash composition of this invention provides the noted advantages due to the presence of the defined anionic surfactant, and because of its specific pH, that is either equal to or greater than about 9, or equal to or less than about 6. As is demonstrated below, conventional wash solutions having the neutral pH (that is, about 7) do not solve the noted problem. Moreover, a wide variety of surfactants were tried, and only those of the recited formula solved the problem.

DETAILS OF THE INVENTION

Figure 1:
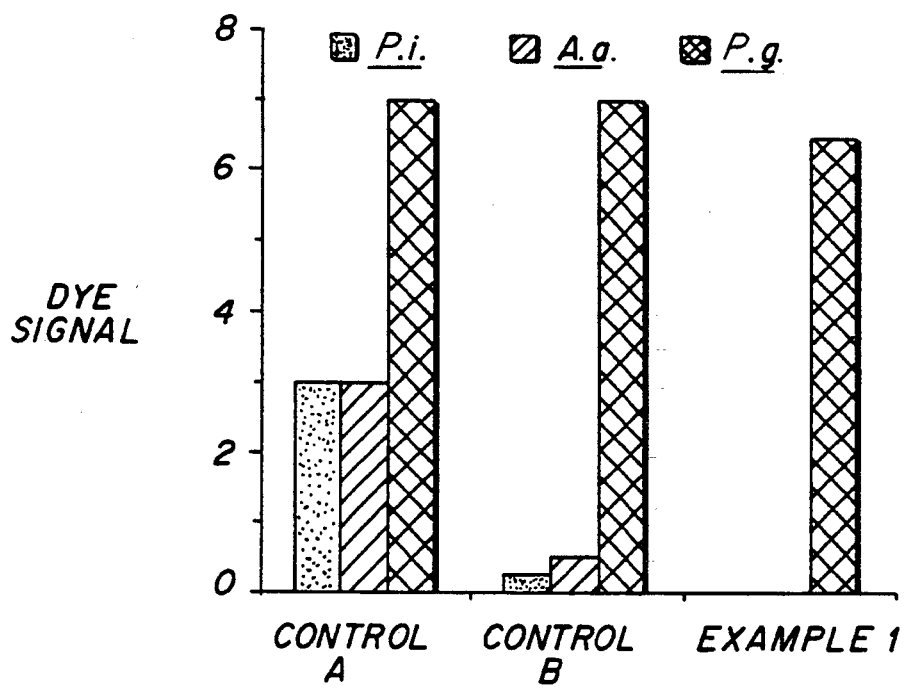
FIG. 1 is a bar graph representation of dye signal data obtained from the assays described in Example 1 below in comparisons with Controls A and B.

The present invention provides a wash composition and diagnostic test kit that can be used in any specific binding assay whereby a ligand of interest is complexed with its corresponding receptor, and uncomplexed materials are removed by washing prior to complex detection. Ligands which can be so complexed are well known in the art and include, but are not limited to, antigenic proteins and carbohydrates, toxins, lectins, drugs, enzymes, steroids, vitamins, polysaccharides, glycolipids, alkaloids, microorganisms, viruses, protozoa, haptens, antibodies, avidin and its derivatives, biotin and its derivatives, nucleic acids, amino acids, peptides, polypeptides, glycopeptides and any components of the foregoing materials. Preferably, this invention is used in the detection of immunological materials which are defined herein as materials, which when injected into an immunocompetent host, will produce an immunological response (that is, cause the production of antibodies specific to those materials), as well as the antibodies so produced.

The method to detect a ligand of interest can be used to assay any human or animal biological fluid or specimen of interest including, but not limited to, whole blood, plasma, sera, lymphatic fluid, bile, urine, spinal fluid, seminal fluid, vaginal secretions, sputum, perspiration, stool specimens, fluid preparations of tissues, periodontal tissue, dental plaque, crevicular fluid and saliva.

It is to be understood that while the remaining discussion is directed to microorganisms associated with periodontal diseases, the use of the kit and wash composition is not so limited. Rather, the following discussion is provided merely for exemplification.

The wash composition of this invention is an aqueous buffered solution which keeps background low, especially when several ligands are being detected simultaneously in the same test device. This is seen in the examples below relating to simultaneous detection of microorganisms associated with periodontal diseases.

The wash composition is buffered to any suitable pH although it is preferred to have either a relatively high pH, that is about 9 or above, or a relatively low pH, that is about 6 or below. More preferably, in the higher pH range, the pH of the composition is from about 9.5 to about 11 with a pH of about 10 being most preferred. If the pH is below about 6, it is preferably in the range of from about 4 to about 6.

The appropriate pH can be provided by the use of an appropriate amount of one or more appropriate buffers (with or without added base or acid, depending upon the pH desired). Organic or inorganic buffers which are well known in the art include, but are not limited to, glycine, phosphate, succinic acid, 2-(4-morpholino)ethanesulfonic acid, 3-(cyclohexylamino)-1-propanesulfonic acid, 3-cyclohexylamino)-2-hydroxy-1propanesulfonic acid, 2-(N-cyclohexylamino)ethanesulfonic acid, and any others which provide buffering at the desired pH and which do not adversely affect the specific binding complex being washed. The amount of each buffer would depend upon its buffering strength and what pH is desired. This could be readily determined by one of ordinary skill in the art, and generally is at least about 0.05 molar. Glycine is a preferred buffer for the high pH range, and succinic acid or 2-(4-morpholino)ethanesulfonic acid is a preferred buffer for the low pH range.

Contained in the wash composition is an essential anionic surfactant which is represented by the formula:

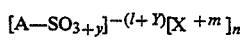

wherein A is a hydrocarbon having a molecular weight of at least about 180, $X^{+m}$ is hydrogen or a monovalent or divalent cation, m is 1 or 2, y is 0 or 1, and n is 1 or 2 provided that m and n are not both 2.

More specifically, in the noted formula, A is a linear, branched or cyclic hydrocarbon having from 13 to 18 carbon atoms, and thus a molecular weight in the range of from about 180 to about 250. Such hydrocarbon groups include, but are not limited to, linear and branched alkyl (for example, tridecyl, tetradecyl, and branched equivalents), cycloalkyl having one or more alkyl substituents (for example, cyclohexyl substituted with linear or branched $C_7$ or higher alkyls or a plurality of lower alkyls) and aromatic carbocycles having one or more alkyl substituents (for example, phenyl substituted with $C_7$ or higher alkyls). When A has more than 16 carbon atoms, it is alkylcyclyl, preferably alkylphenyl. Moreover, in such cases, the cyclyl group can be substituted with more than one alkyl. It is important that the hydrocarbon not be so large that the surfactant loses its water solubility or dispersibility.

In one preferred embodiment, A of the noted formula is an alkyl or alkyl-substituted phenyl having a molecular weight of from about 180 to about 250. The alkyl has from 7 to 12 carbon atoms, and is linear or branched. Useful alkyl groups are, for example, n-octyl, isooctyl, n-decyl, 2,2-diethylbutyl, 2-ethyldecyl and dodecyl. A useful anionic surfactant of this embodiment is available commercially from ARCO under the trademark ULTRAWET 60 L.

In another and more preferred embodiment, the anionic surfactant has the noted formula above wherein A is linear or branched alkyl having from 14 to 16 carbon atoms (for example, tetradecyl, hexadecyl, 2-ethyltetradecyl and 2,2-dimethyltetradecyl). Preferably, A is tetradecyl. One useful anionic surfactant, a tetradecyl sodium sulfate, is commercially available from Union Carbide Corp. under the trademark TERGITOL 4.

Also in the foregoing formula for all preferred embodiments, m and y are both 1, and n is 2.

Generally, $X^{+m}$ is hydrogen or a monovalent or divalent cation from Groups IA or IIA of the Periodic Table, such as alkali metal ions (for example, sodium, potassium and rubidium) and alkaline earth metal ions (for example, magnesium, calcium and strontium). Alkali metal ions such as sodium and potassium ions are preferred. However, the cation can also be an ammonium or an organic cation such as trialkyl- or tetraalkylammonium ions, for example ions formed from di- and triethanolamines, such as di- and tri(2-hydroxyethyl)ammonium, and from trialkylamines, tetramethylammonium and others readily apparent to one skilled in the art, and arylammonium cations such as trimethylphenylammonium and cyclic onion cations, such as 1-methylpyridinium, 3-methylimidazolium and other readily apparent to one skilled in the art.

The anionic surfactant can be present in the wash composition in any amount which is effective to provide the washing needed in a given assay. This amount can vary widely depending upon the concentration of the ligand to be determined, the assay format and the sensitivity of the detection means. Thus, where the ligand is present in high concentration and the detection means is highly sensitive, washing may not be as critical and the anionic surfactant concentration need not be high. Under the opposite conditions, the amount of surfactant desired would be higher. Generally, the amount can be at least about 0.1 percent, based on the composition weight, with from about 1 to about 5 weight percent being more preferred.

Preferred wash compositions also include one or more nonimmunoreactive proteins, such as serum proteins (such as fetal calf serum, bovine serum albumin), casein and other milk proteins, fibrinogen and others readily apparent to one of ordinary skill in the art. These proteins are defined as "nonimmuno-reactive" because they do not participate in the specific binding reactions of the assay. They are present in order to aid in the action of the buffered surfactant in reducing nonspecific binding. They can be present in an amount of at least about 0.1 weight percent, and preferably from about 0.4 to about 0.6 weight percent.

The wash composition can be prepared merely by mixing the anionic surfactant, and optionally nonimmunoreactive protein, in a suitable buffer. It can be used immediately in an assay, or stored in a suitable container for later sale or use, for example as part of a diagnostic test kit.

Such kits can include, in individual packaging or containers, the wash composition and a receptor for the specific binding ligand of interest. The receptor can be water-soluble and detectably labeled (for example with an enzyme or other labeling means) or immobilized on a suitable substrate. Other components of a kit can include detection means such as dye providing compositions (described in more detail below), assay devices, extraction compositions, insolubilizing reagents (described below), instructions, pipettes and other apparatus needed for a typical assay. In a preferred embodiment, the kit includes a disposable test device (described below), and a receptor (for example, an antibody) for the ligand which is immobilized on a particulate substrate, membrane (including polymeric and cellulosic filters), cellulosic sheet or polymeric film. Such a kit can be assembled and sold with all components present, or provided as individual parts prior to use in an assay.

As noted above, the wash composition and test kit can be used in the determination a wide variety of specific binding ligands. In a preferred embodiment, microorganisms associated with periodontal diseases are determined, and the remainder of this description of the assay methods will be directed to that embodiment. In such cases, the ligand to be determined is an antigenic material and the receptor therefor is an antibody.

In particular, the microorganisms *Actinobacillus actinomycetemcomitans*, *Porphyromonas gingivalis* and *Prevotella intermedia* are determined, either individually or collectively, using the present invention. However, other microorganisms which are suspected of being associated with periodontal diseases can also be detected or differentiated with this invention. Such other microorganisms include, but are not limited to, *Wolinella recta*, *Bacteroides forsythus*, *Eikenella corrodens*, *Fusobacterium nucleatum* and *Treponema denticola*. In some embodiments, it is irrelevant as to which serotypes of any of the microorganisms may be present. In other embodiments, the invention can be used to differentiate among serotypes of a single species as well as among species.

The method of this invention is generally qualitative although the amount of specific binding complex can be observed and correlated to the amount of ligand in a specimen. Thus, the assay can be quantitative also. While the ligands determined can be intact microorganisms, it is preferred to extract the ligand (for example a lipopolysaccharide, capsule antigen or outer membrane protein) of interest from the host organism. For periodontal assays, such antigens can be extracted from saliva, mucous from the throat or mouth, human or animal tissue extracts, dental plaque or gingival crevicular fluid.

Antigen extraction from the noted microorganisms can be accomplished using suitable physical or chemical means such as use of a detergent (for example sodium deoxycholate, sodium dodecyl sulfate or sodium decyl sulfate) following known procedures (see U.S. Pat. No. 4,741,999 issued May 3, 1988 to Genco et al), osmotic shock [see for example, Dirienzo et al, *Infect. &*

*Immun.*, 47(1), pp. 31–36, 1985] or sonic means [see for example, Zambon et al, *Infect. & Immun.*, 41(1), pp. 19–27, 1983].

A preferred extraction procedure is demonstrated in Example 1 below using a high pH composition of a cationic surfactant and an anionic surfactant.

If desired, the extracted antigen can be removed from the original specimen, or the original specimen can be suitably diluted with buffer or water, or filtered in order to remove extraneous matter and facilitate complexation of antigen with the corresponding antibody in the assay.

Antibodies useful in the practice of this invention can be monoclonal or polyclonal. Monoclonal antibodies can be prepared using standard procedures, such as those described in U.S. Pat. No. 4,741,999 (note above). Polyclonal antibodies can also be produced using standard procedures, such as described by Zambon et al, supra. Generally, a mammal is immunized one or more times with a suitable quantity of an antigenic component or whole bacterial cells of the organism. After a suitable time, when the titer is acceptable, antisera is recovered from the mammal. Antibodies can be removed from antisera and purified if desired using known procedures and stored in frozen buffered solutions until used. A preferred method for providing highly specific polyclonal antibodies is described in copending U.S. Ser. No. 468,393 (filed Jan. 22, 1990 by Reynolds et al), now abandoned. This method generally calls for injecting a mammal with an immunizing amount of an antigen a first time, injecting the mammal a second time between the second and fourteenth days after the first injection with a boosting amount of the antigen, and beginning the fifteenth day after the first injection, injecting the mammal at least three times every seven day period for at least four seven-day periods with a boosting amount of antigen. An immunizing amount and boosting amount can be readily determined by a skilled worker in the art. After the last booster injection, antisera is removed from the mammal.

After extraction of antigen and provision of antibodies specific to that antigen, the method of this invention is carried out by forming a water-insoluble immunological complex of the antigen and antibody. This complex formation can be accomplished in a number of procedures and the present invention is not limited to a specific procedure even though the "sandwich" assays described in detail below are most preferred.

In one embodiment, the extracted antigen can be insolubilized by direct adsorption or covalent attachment to a solid substrate, such as a particulate substrate (for example, polymeric or glass particles), filtration membranes, cellulosic filter papers, solid polymeric or resin-coated films, glass slides or walls of test tubes, glass or polymeric cuvettes and other substrates readily determinable by one of ordinary skill in the art. Such assays are generally known in the art as "direct binding" assays whereby the antigen directly binds to the substrate, and antibodies are used to complex with the insolubilized antigen. The antibodies can be detectably labeled to make the complex detectable, or the complex can be detected using an anti-antibody which is suitably labeled and specific to the first unlabeled antibody. Detection of the complex can be effected after washing using known techniques. Further details of how direct binding assays are carried out are provided for example in U.S. Pat. No. 4,497,899 (issued Feb. 5, 1985 to Armstrong et al) and copending U.S. Ser. No. 468,045 (filed Jan. 22, 1990 by Snyder et al).

Another embodiment of the method of this invention is an agglutination method whereby antibodies to the extracted antigen are affixed to small particles in some manner and the particles which are detectable by light scattering or by the presence of a tracer such as dye or radioisotope within the particles. The resulting immunoreactive complex is formed through the reaction of antigen with antibodies on the particles, and can be detected using known procedures after washing. Technical details regarding agglutination assays are provided, for example in U.S. Pat. No. 4,847,199 (issued Jul. 11, 1989 to Snyder et al).

Examples of other useful assays include competitive immunoassays and enzyme-linked immunoabsorbent assays (commonly known as ELISA). Such assays are described generally in U.S. Pat. No. 4,427,782 (issued Jan. 24, 1984 to Caldwell et al) and by Schmeer et al, *J. Clin. Microbiol.*, 15(5), pp. 830–834 (1982).

A preferred embodiment of this invention is an immunometric or sandwich assay in which the extracted antigen is reacted at different epitopic sites with two antibodies, one of which is detectably labeled, and the second being immobilized (or capable of being immobilized such as through avidin-biotin complexation or other specific binding reactions). Suitable substrates on which one antibody is immobilized include those noted above for direct binding assays. Preferably, particulate carrier materials formed from organisms, natural or synthetic polymers, glass, ceramics, diatomaceous earth or magnetizable particles are used. These particles are more preferably polymeric, spherical in shape and have an average particle size (in largest dimension) of from about 0.01 to about 10 $\mu$meters, although the size, structural and spatial configurations are not critical. The general procedures for immunometric assays are described, for example, in U.S. Pat. No. 4,376,110 (issued Mar. 8, 1983 to David et al) and U.S. Pat. No. 4,486,530 (issued Dec. 4, 1984 to David et al).

The antibodies can be attached to particulate carrier materials to form water-insoluble immunological reagents by physical or chemical means, including adsorption or covalent reaction with reactive groups on the surface of the materials. Covalent attachment is preferred for better assay sensitivity. Many useful reactive groups are known in the art for antibody attachment, which groups can be part of the chemical structure of the carrier material, or added by coating or chemical treatment of an inert material. One skilled in the art would readily understand how to prepare such materials to have any of the following reactive groups: carboxy, 2-substituted ethylsulfonyl, vinylsulfonyl, epoxy, aldehyde, active halo atoms, amino, hydrazide and active esters such as succinimidoxycarbonyl.

Particularly useful particulate carrier materials are polymeric beads described, for example, in EP-A-0 323 692 (published Jul. 12, 1989) which are prepared from one or more ethylenically unsaturated polymerizable monomers having an active halo atom, activated 2-substituted ethylsulfonyl or vinylsulfonyl groups. Other particularly useful particles having reactive carboxy groups are described in copending U.S. Ser. No. 654,112 (filed Feb. 12, 1991 by Ponticello et al) now U.S. Pat. No. 5,149,737.

Homo- and copolymers described in EP-A-0 323 692 include the following representative materials: poly(m & p-chloromethylstyrene), poly(styrene-co-m & p- chloromethylstyrene-co-2-hydroxyethyl acrylate) (67:30:3 molar ratio), poly[styrene-co-m & p-(2chloroethylsulfonylmethyl)styrene] (96:4 molar ratio), poly{styrene-co-N-[m & p-(2-chloroethylsulfonylmethyl)phenyl]acrylamide} (99.3:0.7 molar ratio), poly(m & d-chloromethylstyrene-co-methacrylic acid) (95:5 molar ratio), poly [styrene-co-m & p- (2-chloroethylsulfonylmethyl)styrene-co-methacrylic acid] (93.5:4.5:2 molar ratio) and poly[styrene-co-4-(2-chloroethylsulfonylmethyl)styrene] (95.5:4.5 molar ratio).

Procedures for attaching antibodies to particles having reactive groups are well known, as described for example in U.S. Pat. No. 3,925,157 (issued Dec. 9, 1975 to Hamsher), U.S. Pat. No. 4,181,636 (issued Jan. 1, 1980 to Fischer), U.S. Pat. No. 4,703,018 (issued Oct. 27, 1987 to Craig et al) and EP-A-0 323 692. In general, the antibodies are mixed with the particles under suitable conditions depending upon the attachment form (adsorption, covalent or use of a linking group). A worker skilled in the art would readily know what conditions should be used for each procedure. For example, for attachment to particles having reactive halo atoms, activated 2-substituted ethylsulfonyl or vinylsulfonyl groups, the antibodies are generally mixed with the particles for up to 24 hours at a temperature of from about 20° to about 40° C. in a suspension buffered at a pH of from about 7 to about 10. If carboxy groups are used for attachment, the well known carbodiimide activators can be used, as well as carbomoylonium compounds are described in EP-A-0 308 235 (published Apr. 22, 1989). Antibodies can be absorbed on particles by incubating particles and antibodies in suspension at suitable temperature for several hours.

More preferably, the immunological reagents described above are coated or deposited on a microporous filtration membrane which is inert to chemical or biological reactions. It is generally composed of one or more natural or synthetic substances which have sufficient integrity for reagents to react or be affixed thereto without loss of form or function. It is porous enough for filtration needed to remove substantially all uncomplexed materials from the complexes formed thereon. Useful membrane materials include, but are not limited to, porous natural or synthetic polymers, sintered glass, membranes of glass or polymeric films or fibers, ceramic materials, cellulosic materials and particulate structures composed of beads bound together with an adhesive or binder material. The membranes are generally flat, but some irregularities in the surfaces are acceptable, as well as some curvature if it is desired. One skilled in the art would be able to identify other useful materials which are commercially available or prepared using known techniques. Particularly useful materials are treated or untreated polyamide microporous membranes such as those commercially available from Pall Corp. under the trademarks LOPRODYNE and BIODYNE.

The membrane generally has an average pore size in the largest dimension of from 0.5 to about 5 µmeters, although smaller or larger pores would be acceptable as long as the complexes formed remain on the membrane and fluid drainage is not adversely affected.

If desired, the membrane can be coated with surfactant or nonimmunoreactive protein (such as casein or succinylated casein), as known in the art to reduce nonspecific interactions or to promote desired filtration.

The water-insoluble immunological reagents having appropriate antibodies can be affixed to the membrane over its entire surface or in defined regions thereof. Affixation is accomplished using any mechanical means such as coating, dipping, printing or spraying or fixed by covalent means. Generally, they are coated and dried on the membrane prior to use. They can be used in admixture with hydrophilic binders to provide additional integrity to the coating.

The membrane can be hand held in the assay to provide sites for complexation of extracted antigen and the antibodies thereon. However, preferably, the membrane is disposed or mounted in a disposable test device or article having a suitable frame and structure for holding the membrane and fluid which is drained therethrough. Many such test devices are known in the art, including but not limited to those shown in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike), U.S. Pat. No. 4,446,232 (issued May 1, 1984 to Liotta), U.S. Pat. No. 4,833,087 (issued May 23, 1989 to Hinckley), U.S.-Pat. No. 4,847,199 (issued Jul. 11, 1989 to Snyder et al), U.S. Pat. No. 4,921,677 (issued May 1, 1990 to Hinckley et al) and U.S. Pat. No. 4,923,680 (issued May 8, 1990 to Nelson). Particularly useful test devices are those marketed by Eastman Kodak Company under the trademark SURECELL test devices.

Preferred test devices have three test wells designed for providing both negative and positive control results as well as a specimen test result. Each test well contains a membrane as described herein.

Once the water-insoluble complex of antigen and antibodies is formed (preferably on the membrane), the complex is washed with the wash composition of this invention to remove uncomplexed materials prior to detection of the complex. If the complex is on a substrate that does not allow fluid drainage, the uncomplexed materials and fluid can be decanted off or otherwise removed. Where a membrane or filter is used, the fluid and uncomplexed materials flow through the membrane or filter and the complex of interest is left thereon.

Depending upon the means of detection, the water-insoluble complex can then be detected using a number of standard reagents and methods. For example, the complex may be detected without tracers or signal producing labels using light scattering techniques known in the art. Agglutinates can be similarly detected.

Preferably, however, whether the assay format is a direct binding assay or immunometric assay, the immunological complex is detected by means of a detectable label on the water-soluble receptor (such as an antibody). Such labels can include, but are not limited to enzymes, avidin, biotin, radioisotopes, fluorogens and chromogens. Enzymes are preferred and can be used to generate colorimetric, fluorometric or chemiluminescent signals which can be evaluated with the unaided eye or using standard spectrophotometric equipment to measure electromagnetic density, spectra or intensity. Useful enzymes include, but are not limited to peroxidase, urease, alkaline phosphatase, acid phosphatase, glucose oxidase, $\beta$-galatosidase, glucosidase and others readily apparent to one skilled in the art. Alkaline phosphatase and peroxidase are preferred with peroxidase being most preferred.

For a given enzyme label, there are various known compositions which provide detectable colorimetric, fluorometric or chemiluminescent signals in the presence of the enzyme. For example, one preferred embodiment utilizes a dye-providing composition which provides a dye in the presence of the enzyme through one or more chemical reactions. A number of leuco dyes are known to be useful for this purpose where peroxidase is the label including those described in U.S. Pat. No. 4,089,747 (issued May 16, 1978 to Bruschi) and U.S. Pat. No. 4,670,386 (issued Jun. 2, 1987 to Babb et al). A preferred dye-providing composition is illustrated in the examples below.

Alternatively, the enzyme label can be used in one or more reactions to produce a chemiluminescent signal, such as described for example in U.S. Pat. No. 4,647,532 (issued Mar. 3, 1987 to Watanabe et al), U.S. Pat. No. 4,835,101 (issued May 30, 1989 to Kao et al), U.S. Pat. No. 4,729,950 (issued Mar. 8, 1988 to Kricka et al) and U.S. Pat. No. 4,598,044 (issued Jul. 1, 1986 to Kricka et al). Other labels besides enzymes can also be used to produce chemiluminescent signals.

In the preferred immunometric assay, at some point the antigen is contacted with a detectably labeled water-soluble antibody. This can occur prior to, simultaneously with or subsequent to the formation of the immunological complex, but generally prior to washing with the wash composition of this invention. Thus, the complex of antigen and two antibodies is left on the preferred membrane when uncomplexed materials are washed through. Following formation of this sandwich complex and washing, detection is carried out using reagents and procedures described generally above.

Positive or negative controls can be carried out simultaneously with assay of the specimen. Depending upon the signal being produced for detection, appropriate reagents can be added to stop signal production, for example by adding reagents to stop the formation of a dye or production of light by chemiluminescence. These materials are well known in the art.

In a preferred method for the determination of a microorganism associated with periodontal disease, the method comprises the steps of:

A. contacting an aqueous specimen suspected of containing an antigen extracted from a microorganism associated with periodontal disease with a microporous filtration membrane having thereon, in a discrete zone of a surface of the membrane, a water-insoluble reagent comprising water-insoluble particles having affixed thereto antibodies specific to the antigen,
to form, in the zone, a water-insoluble complex between the antibody and the antigen, B. contacting the water-insoluble complex with a detectably labeled second antibody specific to the antigen to form a detectably labeled, water-insoluble sandwich complex in the zone, C. simultaneously or subsequently to step B, separating uncomplexed materials from the labeled, water-insoluble sandwich complex by washing the uncomplexed materials through the membrane with the aqueous wash composition described herein,
to separate uncomplexed materials from the labeled, water-insoluble sandwich complex, and D. detecting the labeled, water-insoluble sandwich complex as a determination of the microorganism in the specimen.

More preferably, the method just described is useful for the simultaneous determination or differentiation of a plurality of such microorganisms wherein the membrane has a plurality of distinct and independent zones containing distinct water-insoluble reagents for each of the specific microorganisms of interest. Any or all of the microorganisms *Actinobacillus actinomycetemcomitans, Prevotella intermedia* and *Porphyromonas gingivalis* can be determined in this manner.

Another embodiment of this invention is an immunoassay for detecting the presence or amount of a water-insoluble complex formed from an antigen extracted from a microorganism associated with periodontal disease and an antibody specific to the antigen, comprising:

A. separating the water-insoluble complex from uncomplexed materials by washing with the aqueous wash composition described herein, and B. detecting the separated water-insoluble complex or the uncomplexed materials washed from the complex.

Uncomplexed materials can be readily determined using various reagents known in the art depending upon the particular immunoassay format. For example, if uncomplexed antibody is to be detected, it can be complexed with a known quantity of labeled antigen. The amount of antibody can then be determined and correlated to the amount of unknown antigen in the original specimen.

The following examples are included to illustrate the practice of this invention, and are not meant to be limiting in any way. All percentages are by weight unless otherwise noted.

In all of the Figures, the bar graphs represent dye signals resulting from immunological reaction of the extracted antigen with the three antibody reagents present. For acceptable assays, the antigen should react only with its corresponding antibody, but if there is cross-reactivity due to non-specific binding of antigen to antibodies, unwanted dye signals will result.

Materials and Methods for Examples:

SURECELL ™ disposable test devices were used containing LOPRODYNE ™ nylon microporous filtration membranes (1.2 $\mu$meters average pore size) incorporated into the three test wells. The membrane was used without any further treatment.

A dye-providing composition A was prepared to include 4,5-bis(4-methoxyphenyl)-2-(3,5-dimethoxy-4-hydroxyphenyl)imidazole leuco dye (0.008%), poly(vinyl pyrrolidone) (1%), sodium phosphate buffer (10 mmolar, pH 6.8), hydrogen peroxide (10 mmolar), 4'-hydroxyacetanilide (0.5 mmolar) and diethylenetriaminepentaacetic acid (10 $\mu$molar). Dye-providing composition B was the same but contained 5 mmolar 4'-hydroxyacetanilide.

The dye stop solution comprised sodium azide (0.1%) in phosphate buffered saline solution.

Various wash compositions were tried, as described below.

Polyclonal antibodies directed against each of the three microorganisms *Actinobacillus actinomycetemcomitans, Bacteroides intermedius* and *Bacteroides gingivalis* were prepared by intravenous injection of rabbits according to the protocol described in U.S. Ser. No. 468,393 (noted above). IgG fractions were prepared by ammonium sulfate precipitation, and stored at 4° C. in phosphate buffered saline solution (0.3–0.4% solution). The bacterial strains used to produce the antisera were supplied as viable cultures by H. S. Reynolds (SUNY, Buffalo School of Dentistry). Isolates were subcultured on anaerobic plates. The microorganisms were those identified by the deposit numbers of ATCC 43717, ATCC 43718 and ATCC 43719 for *Actinobacillus ac-* tinomycetemcomitans (A.a.) (serotypes A, B and C, respectively), ATCC 25611, NCTC 9336 and ATCC 49046 for *Prevotella intermedia* (P.i.) (serotypes A, B and C, respectively) and ATCC 33277, ATCC 53978 and ATCC 53977 for Porphyromonas gingivalis (P.g.) (serotypes A, B and C, respectively). ATCC is the American Type Culture Collection in Rockville, Md., and the NCTC is the National Collection of Type Cultures in London, England.

Water-insoluble reagents were prepared by covalently binding the antibodies to polymeric particles (1μ meter average diameter) of poly[styrene-co-4-(2-chloroethylsulfonylmethyl)styrene] (95.5:4.5 molar ratio) which had been prepared using the procedures of EP-A-0 323 692 (noted above). Covalent attachment was achieved by adding the antibodies to a solution of borate buffer (0.05 molar, pH 8.5) in a test tube and mixing well. The amount of A.a. used was 0.52 mg/ml (all serotypes) with each serotype being about 0.17 mg/ml. The amount of P.i. and P.g. used was about 0.75 mg/ml each, with each serotype of each microorganism being about 0.25 mg/ml. The polymeric particles (3% solids) were added to the buffered mixture, and the resulting suspension was rotated end-over-end for 4 hours at room temperature to allow covalent attachment of the antibodies to the particles. The suspension was then centrifuged at 2800 rpm for 10 minutes. The supernatant was discarded and the pellet was suspended in glycine buffer (0.1%, pH 8.5) containing TWEEN TM 20 nonionic surfactant (0.1%, ICI Americas) and merthiolate (0.01%).

A coating suspension of the reagent described above (0.35% solids) was prepared to have polyacrylamide binder (5%), TWEEN TM 20 nonionic surfactant (0.1%), merthiolate (0.01%) and UVITEX TM optical brightener (0.0005%, Ciba-Geigy) in glycine buffer (0.1 molar, pH 8.5). Each reagent directed to a distinct antigen was coated in defined regions of the membrane in the test devices described above.

Enzyme-antibody conjugates were prepared using antibodies directed to each microorganism conjugated to horseradish peroxidase using the procedure of Yoshitake et al, *Eur. J. Biochem.*, 101, 395, 1979. Each conjugate composition comprised the conjugates (about 7.5–15 μg of each per ml) added to a solution of casein [0.5%, from a 1% solution in 0.1 molar 3-(N-morpholino)propanesulfonic acid buffer, pH 7.5], TWEEN TM 20 nonionic surfactant (0.3%), merthiolate (0.01%) and 4'-hydroxyacetanilide (10 mmolar) in buffer (0.1 molar, pH 7.5). The solution was filtered through a 0.22 μmeter filter.

The composition for extracting antigen from the microorganisms comprised EMCOL TM CC-9 cationic surfactant (5%, Witco Corp.), sodium dodecyl sulfate (5%) in glycine buffer (0.1 molar, pH 8.5).

Various surfactants used in the comparisons of wash compositions below were as follows:

TERGITOL TM 4 alkylsodium sulfate anionic surfactant available from Union Carbide Corp.

EMPHOS TM CS1361 phosphate ester available from Witco Corp.

AVANEL TM S-70 sodium alkyl ether sulfonate anionic surfactant available from PPG/Mazer.

DUPONOL TM WAQE sodium lauryl sulfate anionic surfactant and ZONYL TM fluorochemical anionic surfactant available from E. I. DuPont de Nemours & Co.

ULTRAWET TM 60L linear alkylate sulfonate organic salt anionic surfactant available from ARCO.

MONAWET TM MM80 dihexyl sodium sulfosuccinate anionic surfactant available from Mona Industries.

SARKOSYL TM NL sodium lauryl sarcosinate anionic surfactant available from Ciba-Geigy Corp.

AEROSOL TM AY100 diamyl ester of sodium sulfosuccinic acid anionic surfactant available from American Cyanamide.

TRITON TM 770 sodium salt of an alkylarylpolyether sulfate anionic surfactant and TRITON TM OS44 phosphate anionic surfactant available from Rohm and Haas.

HOSTAPAL TM BV alkylarylpolyglycol ether sulfate, sodium salt anionic surfactant available from American Hoechst Corp.

POLYSTEP TM B12 sodium lauryl ether sulfate anionic surfactant available from Stepan Co.

SULFOBETAINE TM DCH alkylammonium sulfonate, inner salt zwitterionic surfactant available from Textilana Corp.

All other reagents were obtained from Eastman Kodak Company or other well known suppliers of chemicals and reagents.

EXAMPLE 1

Sandwich Assay Using Wash Composition of Invention

This example demonstrates the method of this invention to significantly reduce background in sandwich assays for microorganisms associated with periodontal diseases. It also shows the importance of the pH of the wash composition by comparisons with Control assays using wash compositions at about pH 7.

Wash Composition

The wash composition used in the method of this invention was composed of TERGITOL TM 4 anionic surfactant (2.7%) in phosphate buffer (0.1 molar, pH 10). Control A assay was carried out using a solution of sodium decyl sulfate (1.8%) in sodium phosphate buffer (0.1 molar, pH 7.3) as the wash solution. Control B assay was carried out using TERGITOL TM 4 anionic surfactant (2.7%) in phosphate buffer at pH 7.2.

Assay Procedure

This assay procedure was used generally in all of the examples of this specification with modifications being noted.

Antigen from ATCC 53978 [serotype B, P.g.] was extracted by subjecting the cells to the extraction composition noted above for less than one minute at room temperature to achieve a final concentration of $1.25 \times 10^8$ total cells/ml.

The extract (450 μl) was filtered through a 1.2 μmeter membrane and added to one test well of the test device described above. The membrane of the test device had defined regions of reagents specific for each of A.a., P.g. and P.i. Fluid was allowed to drain through the membrane in the test well. Antibody conjugate composition (80 μl) was immediately added to each test well followed by incubation for two minutes at room temperature (about 20–25° C.). The wash solution (500 μl) was then added to each test well and allowed to drain, followed by a second wash (500 μl).

Dye-providing composition A (80 μl) was added to each test well followed by a one minute incubation at room temperature. The dye signal was then visually evaluated and compared to a calibrated color chart containing reflectance density values. The reflection densities were then converted to transmission density ($D_T$) using the Williams-Clapper transformation [see *J. Optical Soc. Am.*, 43, p. 595 (1953)]. $D_T$ values of 0.003 or less correspond to a visual evaluation of "no dye signal".

The results were then tabulated as follows and plotted on bar graphs as shown in FIG. 1. It is clear that only the wash composition used according to the present invention effectively reduced the background from cross-reactivity of the P.g. antigen with antibodies specific to A.a. and P.i. The background was too high because some B.g. antigen reacted non-specifically with A.a. and B.i. antibodies in the Control assays. This example indicates that the wash composition should have pH above about 9.

TABLE I

| Assay | $D_T$ Dye Signal | | |
|---|---|---|---|
| | P.g. Reagent | P.i. Reagent | A.a. Reagent |
| Control A | 0.114 | 0.024 | 0.024 |
| Control B | 0.114 | 0.005 | 0.007 |
| Example 1 | 0.101 | 0.003 | 0.003 |

EXAMPLE 2

Comparative Assays at High pH Using Different Surfactants

This example is similar to Example 1 except that the wash compositions used in the assays were at pH 10.

The Control A assay was the same as in Example 1. The Control C assay used sodium decyl sulfate (1.8%) in phosphate buffer (0.1 molar, pH 10), whereas the Control D assay used sodium decyl sulfate (10%) in the same buffer. The Example 2 assay was the same as the Example 1 assay.

Figure 2:
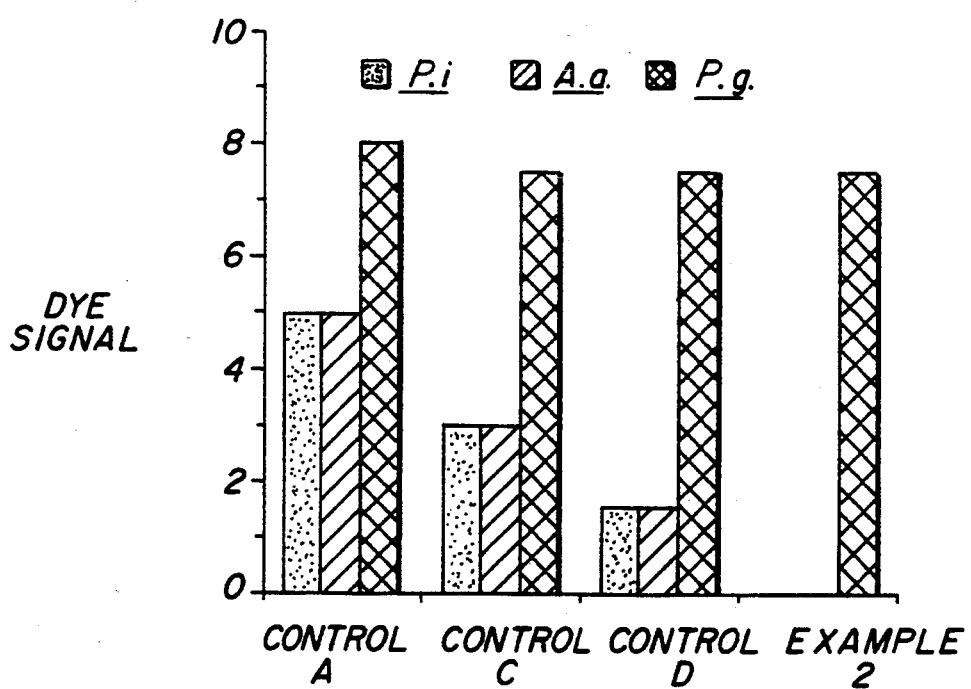
FIG. 2 is a bar graph representation of dye signal data obtained from the assays described in Example 2 below in comparisons with Controls A, C and D.

The results of the assays are shown below in Table II and graphically represented in FIG. 2. It is clear that only the assay of this invention provided detection of the antigen from P.g. without significant background from cross-reactivity of the antigen with antibodies specific to the other microorganisms. The Control assays demonstrated unacceptably high cross-reactivity and consequently high background. This indicates that besides pH, the wash composition must include certain surfactants.

TABLE II

| Assay | $D_T$ Dye Signal | | |
|---|---|---|---|
| | P.g. Reagent | P.i. Reagent | A.a. Reagent |
| Control A | 0.175 | 0.057 | 0.057 |
| Control C | 0.145 | 0.024 | 0.024 |
| Control D | 0.145 | 0.015 | 0.015 |
| Example 2 | 0.145 | 0.003 | 0.003 |

EXAMPLE 3

Comparative assays Using Cationic and Nonionic Surfactants in the Wash Compositions This example is a comparison of several assays carried out by the protocol of Example 1 but using a variety of wash compositions.

The Control A and B assays were like those described above. Example 3 was like the Example 1 assay. The other Control assays utilized the following wash compositions:

Control E: EMCOL TM CC9 cationic surfactant (10%) in phosphate buffer (0.1 molar, pH 7.2).
Control F: EMCOL TM CC9 cationic surfactant (10%) in phosphate buffer (0.1 molar, pH 10).
Control G: TWEEN TM 20 nonionic surfactant (10%) in phosphate buffer (0.1 molar, pH 7.2).
Control H: TWEEN TM 20 nonionic surfactant (10%) in phosphate buffer (0.1 molar, pH 10).

Figure 3:
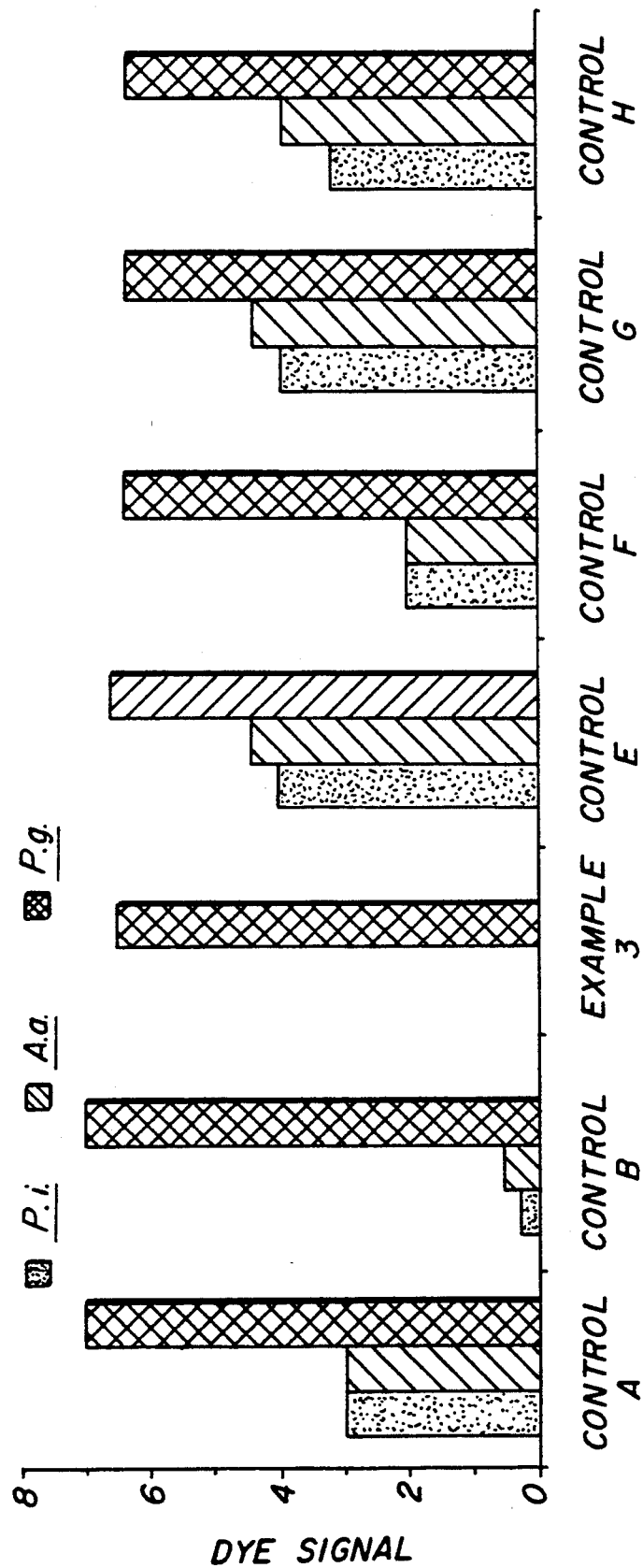
FIG. 3 is a bar graph representation of dye signal data obtained from the assays described in Example 3 below in comparisons with A, B and E-H.

Table III below shows the results of the assays, and the results are graphically represented in FIG. 3. It is apparent that only Example 3 demonstrates accurate detection of the extracted antigen (from P.g.) without significant cross-reactivity with the antibodies specific to the other microorganisms.

TABLE III

| Assay | $D_T$ Dye Signal | | |
|---|---|---|---|
| | P.g. Reagent | P.i. Reagent | A.a. Reagent |
| Control A | 0.114 | 0.024 | 0.024 |
| Control B | 0.114 | 0.005 | 0.007 |
| Control E | 0.180 | 0.057 | 0.073 |
| Control F | 0.175 | 0.022 | 0.022 |
| Control G | 0.175 | 0.057 | 0.073 |
| Control H | 0.175 | 0.027 | 0.057 |
| Example 3 | 0.101 | 0.003 | 0.003 |

EXAMPLES 4 & 5

Comparisons of Various Wash compositions Containing Anionic Surfactants

These examples follow the assay protocol described in Example 1 and compare a number of wash compositions containing, primarily, anionic surfactants.

The antigen determined was extracted from serotype C of P.g. The Example 4 and Control A assays were like those described in Example 1 except that Example 4 was in 3-cyclohexylamino-2-hydroxy-1-propanesulfonic acid buffer (0.1 molar, pH 10). The Example 5 assay used a wash composition comprising ULTRAWET TM 60L anionic surfactant (5%) in the same buffer (0.1 molar, pH 10). All of the remaining control assays used wash compositions comprising the following surfactants in 3-cyclohexylamino-2-hydroxy-1-propanesulfonic acid buffer (0.1 molar, pH 10):

Control I: EMPHOS TM CS1361 anionic surfactant (5%).
Control J: AVANEL TM S-70 anionic surfactant (5%).
Control K: ethanolamine nonionic surfactant (3%).
Control L: DUPONOL TM WAQE anionic surfactant (5%).
Control M: ZONYL TM FSJ anionic surfactant (5%).
Control N: MONAWET TM MM80 anionic surfactant (5%).
Control O: SARKOSYL TM NL anionic surfactant (5%).
Control P: AEROSOL TM AY100 anionic surfactant (5%).
Control Q: TRITON TM 770 anionic surfactant (5%).

Figure 4:
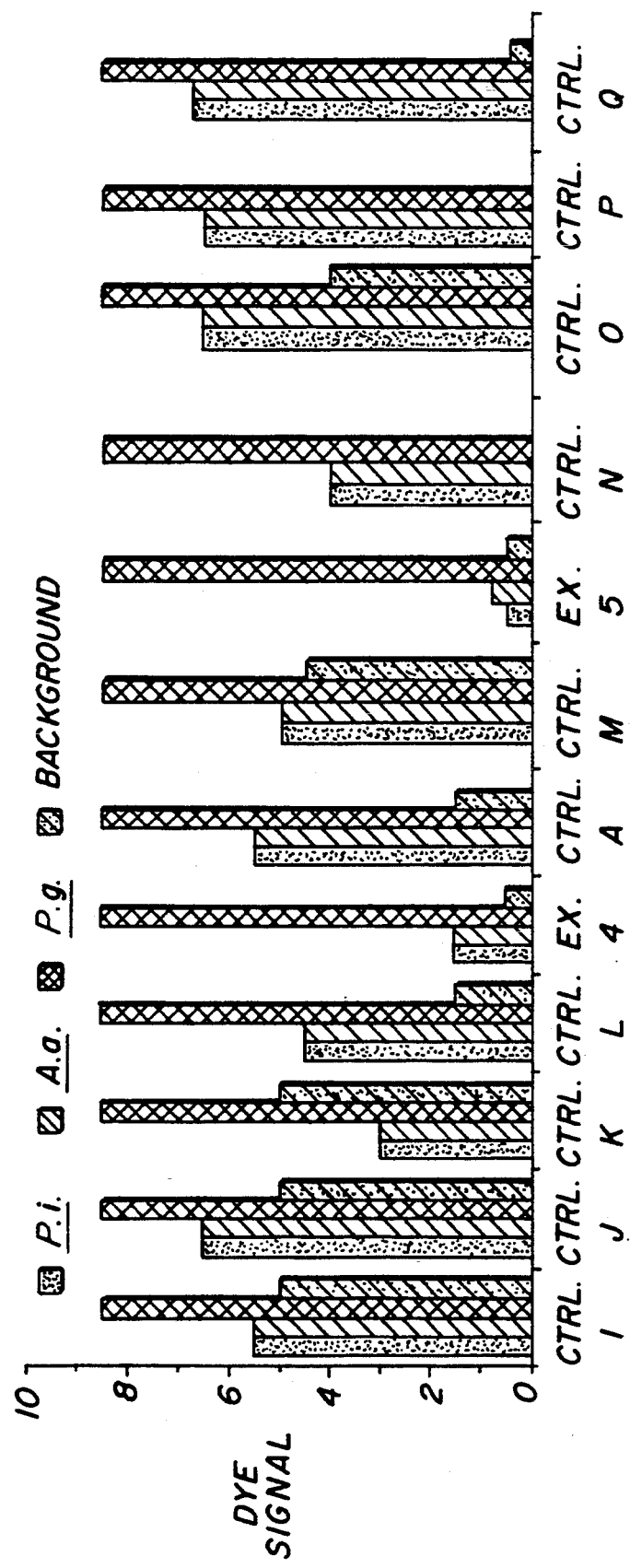
FIG. 4 is a bar graph representation of dye signal data obtained from the assays described in Examples 4 and 5 below in comparisons with Controls A and I-Q.

The assay results are shown in Table IV below and graphically illustrated in FIG. 4. Only the assays of the present invention provided sensitive detection of the extracted antigen (from p.q.) without significant cross-reactivity with the antibodies specific for the other microorganisms. The background signals shown in FIG. 4 are from signal not associated with antigen-antibody binding.

TABLE IV

| Assay | $D_T$ Dye Signal | | |
|---|---|---|---|
| | P.g. Reagent | P.i. Reagent | A.a. Reagent |
| Control A | 0.185 | 0.073 | 0.073 |
| Control I | 0.185 | 0.073 | 0.073 |
| Control J | 0.185 | 0.101 | 0.101 |
| Control K | 0.185 | 0.114 | 0.114 |
| Control L | 0.185 | 0.042 | 0.042 |
| Control M | 0.185 | 0.057 | 0.057 |
| Control N | 0.185 | 0.027 | 0.027 |
| Control O | 0.185 | 0.101 | 0.101 |
| Control P | 0.185 | 0.101 | 0.101 |
| Control Q | 0.185 | 0.108 | 0.108 |
| Example 4 | 0.185 | 0.015 | 0.015 |
| Example 5 | 0.185 | 0.007 | 0.009 |

EXAMPLES 6-8

Further Comparative Assays Using Anionic Surfactants

These examples were carried out following the protocol described in Example 1 for all assays. Control A was as described above. All wash compositions contained the noted surfactants in 3-cyclohexylamino-2-hydroxyl-1-propanesulfonic acid buffer (0.1 molar, pH 10):

Example 6: ULTRAWET TM 60L anionic surfactant (5%).

Example 7: Mixture of ULTRAWET TM 60L anionic surfactant (5%) and TERGITOL TM 4 anionic surfactant (5%).

Example 8: TERGITOL TM 4 anionic surfactant (2.7%).

Control R: TRITON TM QS44 anionic surfactant (5%).

Control S: HOSTAPAL TM BV anionic surfactant (5%).

Control T: POLYSTEP TM B12 anionic surfactant (5%).

Control U: SULFOBETAINE TM zwitterionic surfactant (5%).

Figure 5:
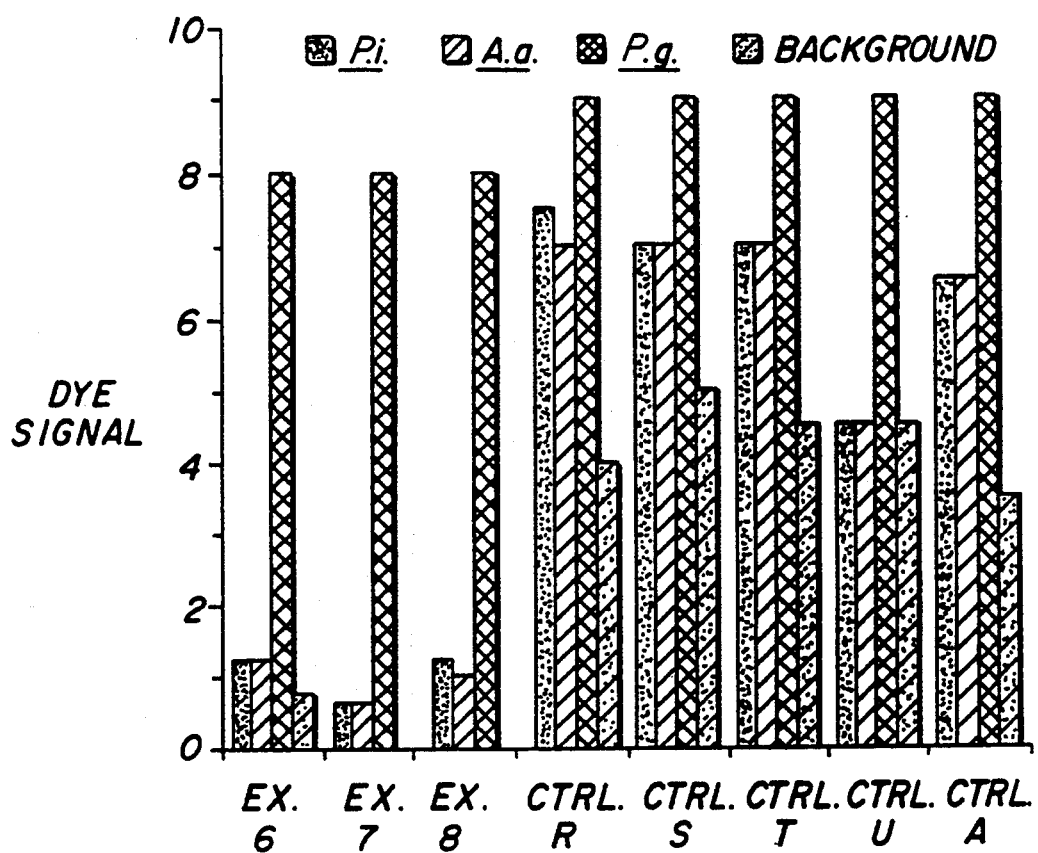
FIG. 5 is a bar graph representation of dye signal data obtained from the assays described in Examples 6-8 below in comparisons with Controls A and R-U.

The results of the assays are shown in Table V below and illustrated in the bar graphs of FIG. 5. It is apparent that only the assays of this invention provided the desired sensitivity to the extracted antigen from P.g. with significantly reduced cross-reactivity to the antibodies specific to the other microorganisms. The background signal in FIG. 5 was from signal not associated with antigen-antibody binding.

TABLE V

| Assay | $D_T$ Dye Signal | | |
|---|---|---|---|
| | P.g. Reagent | P.i. Reagent | A.a. Reagent |
| Control A | 0.195 | 0.101 | 0.101 |
| Control R | 0.195 | 0.145 | 0.114 |
| Control S | 0.195 | 0.114 | 0.114 |
| Control T | 0.195 | 0.114 | 0.114 |
| Control U | 0.195 | 0.042 | 0.042 |
| Example 6 | 0.175 | 0.013 | 0.013 |
| Example 7 | 0.175 | 0.009 | 0.009 |
| Example 8 | 0.175 | 0.011 | 0.011 |

EXAMPLE 9

Comparison of Similar Surfactants in Wash Compositions

This example compares three similar surfactants in wash compositions in assays carried out using the protocol of Example 1. TERGITOL TM 4 anionic surfactant (2.7%) in 3-cyclohexylamino-2-hydroxypropanesulfonic acid buffer (0.1 molar, pH 10) was used in the practice of this invention (Example 9), and was compared to the use of wash compositions containing TERGITOL TM 7 anionic surfactant (Control V, 0.5%) and TERGITOL TM 8 anionic surfactant (Control W, 5%) in glycine buffer (pH 10). At 5% concentration, TERGITOL TM 7 anionic surfactant did not flow through the membrane. It is generally an alkylsulfate having about 17 carbon atoms, and TERGITOL TM 8 anionic surfactant is generally an alkylsulfate having about 18 carbon atoms. Both are available from Union Carbide.

The results of the assays are shown below in Table VI. It is clear that the similar surfactants do not provide the sensitivity and low cross reactivity desired and achieved using the wash composition containing TERGITOL TM 4 anionic surfactant.

TABLE VI

| Assay | $D_T$ Dye Signal | | |
|---|---|---|---|
| | P.g. Reagent | P.i. Reagent | A.a. Reagent |
| Control V | 0.175 | NA | 0.019 |
| Control W | 0.175 | 0.024 | 0.025 |
| Example 9 | 0.175 | 0.011 | 0.011 |

NA = Not Available

EXAMPLES 10-16

Preferred Wash Compositions and Assays Using Same

A preferred wash composition of this invention includes casein mixed with TERGITOL TM 4 anionic surfactant in an appropriate buffer. The protocol of these assays was that as described in Example 1. The following wash compositions of this invention were used:

Example 10: Surfactant (5%) only in succinic acid (0.1 molar, pH 5).

Example 11: Surfactant (5%) only in 2-(4-morpholino)ethanesulfonic acid buffer (0.1 molar, pH 6).

Example 12: Surfactant (5%) and casein (0.5%) in 2-(4-morpholino)ethanesulfonic acid buffer (0.1 molar, pH 6).

Example 13: Surfactant (5%) only in glycine buffer (0.1 molar, pH 9).

Example 14: Surfactant (5%) and casein (0.5%) in glycine buffer (0.1 molar, pH 9).

Example 15: Surfactant (5%) only in glycine buffer (0.1 molar, pH 10).

Example 16: Surfactant (5%) and casein (0.5%) in glycine buffer (0.1 molar, pH 10).

Figure 6:
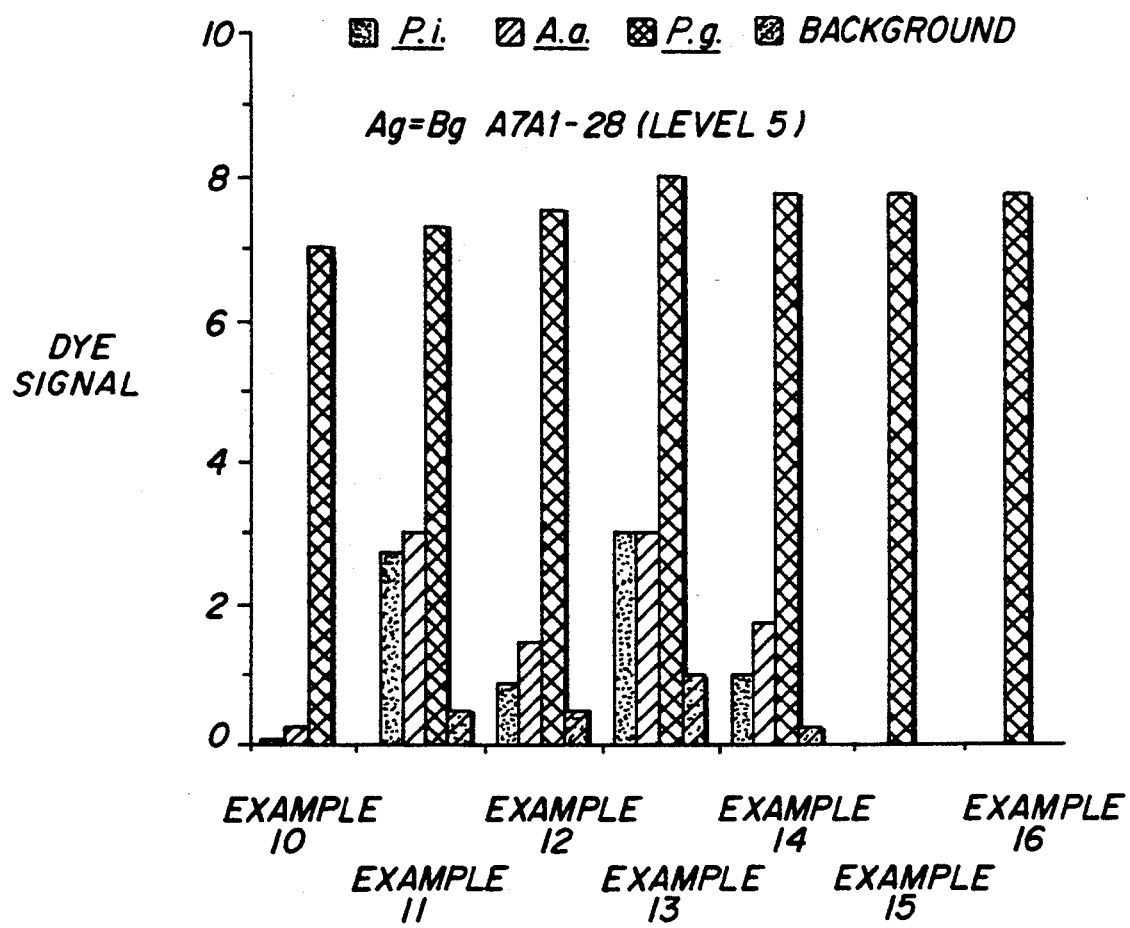
FIG. 6 is a bar graph representation of dye signal data obtained from the assays described in Examples 10-16 below using various wash compositions of this invention.

The results of the assays are shown in the following Table VII and graphically illustrated in FIG. 6. The presence of casein seems to reduce cross-reactivity in assays using wash compositions that have pH closer to neutral. As the pH becomes more acidic (5 or below) or more basic (10 or above), the casein has less effect. The background signal in FIG. 6 was from dye signal not associated with antigen-antibody binding.

TABLE VII

| Assay | $D_T$ Dye Signal | | |
|---|---|---|---|
| | P.g. Reagent | P.i. Reagent | A.a. Reagent |
| Example 10 | 0.114 | 0.003 | 0.005 |
| Example 11 | 0.130 | 0.023 | 0.024 |
| Example 12 | 0.145 | 0.011 | 0.015 |
| Example 13 | 0.175 | 0.024 | 0.024 |

TABLE VII-continued

| | $D_T$ Dye Signal | | |
|---|---|---|---|
| Assay | P.g. Reagent | P.i. Reagent | A.a. Reagent |
| Example 14 | 0.160 | 0.011 | 0.017 |
| Example 15 | 0.160 | 0.003 | 0.003 |
| Example 16 | 0.160 | 0.003 | 0.003 |

$6.25 \times 10^7$ cells/ml, $3.91 \times 10^6$ cells/ml and $4.88 \times 10^5$ cells/ml for A.a.

The results of the assays are tabulated in Table VIII. They illustrate the improved results obtained by using the method of this invention, and that the use of a protein pretreatment aids in the elimination of cross-reactivity particularly when high antigen concentrations are used.

TABLE VIII

| | | | $D_T$ Dye Signal | | |
|---|---|---|---|---|---|
| Antigen | Cell Concentration | Assay | P.g. Reagent | P.i. Reagent | A.a. Reagent |
| P.g. Serotype A | $1.25 \times 10^8$ cells/ml | Control | 0.175 | 0.089 | 0.089 |
| | | Example 17 | 0.175 | 0.007 | 0.011 |
| P.g. Serotype A | $1.56 \times 10^7$ cells/ml | Control | 0.101 | 0.019 | 0.019 |
| | | Example 17 | 0.114 | 0.003 | 0.003 |
| P.g. Serotype A | $1.95 \times 10^6$ cells/ml | Control | 0.020 | 0.003 | 0.003 |
| | | Example 17 | 0.019 | 0.003 | 0.003 |
| P.g. Serotype C | $1.25 \times 10^8$ cells/ml | Control | 0.185 | 0.101 | 0.101 |
| | | Example 17 | 0.185 | 0.003 | 0.003 |
| P.g. Serotype C | $1.56 \times 10^7$ cells/ml | Control | 0.114 | 0.022 | 0.022 |
| | | Example 17 | 0.160 | 0.003 | 0.003 |
| P.g. Serotype C | $1.95 \times 10^6$ cells/ml | Control | 0.025 | 0.003 | 0.003 |
| | | Example 17 | 0.011 | 0.003 | 0.003 |
| P.g. Serotype B | $1.25 \times 10^8$ cells/ml | Control | 0.175 | 0.057 | 0.057 |
| | | Example 17 | 0.195 | 0.003 | 0.003 |
| P.g. Serotype B | $1.56 \times 10^7$ cells/ml | Control | 0.101 | 0.007 | 0.007 |
| | | Example 17 | 0.114 | 0.003 | 0.003 |
| P.g. Serotype B | $1.95 \times 10^6$ cells/ml | Control | 0.022 | 0.003 | 0.003 |
| | | Example 17 | 0.024 | 0.003 | 0.003 |
| P.i. Serotype A | $1.25 \times 10^8$ cells/ml | Control | 0.022 | 0.195 | 0.022 |
| | | Example 17 | 0.003 | 0.175 | 0.003 |
| P.i. Serotype A | $1.56 \times 10^7$ cells/ml | Control | 0.003 | 0.145 | 0.003 |
| | | Example 17 | 0.003 | 0.114 | 0.003 |
| P.i. Serotype A | $1.95 \times 10^6$ cells/ml | Control | 0.003 | 0.054 | 0.003 |
| | | Example 17 | 0.003 | 0.024 | 0.003 |
| A.a. Serotype B | $6.25 \times 10^7$ cells/ml | Control | 0.003 | 0.003 | 0.175 |
| | | Example 17 | 0.003 | 0.003 | 0.175 |
| A.a. Serotype B | $3.91 \times 10^6$ cells/ml | Control | 0.003 | 0.003 | 0.089 |
| | | Example 17 | 0.003 | 0.003 | 0.101 |
| A.a. Serotype B | $4.88 \times 10^5$ cells/ml | Control | 0.003 | 0.003 | 0.007 |
| | | Example 17 | 0.003 | 0.003 | 0.011 |

EXAMPLE 17

Assays of the Invention Determining Various Concentrations of Antigen, With and Without Protein Pretreatment The present example illustrates the practice of this invention to determine various concentrations of antigen extracted from A.a, P.g. and P.i. The assay was carried out using the protocol described in Example 1 except that the solutions of extracted antigen were mixed with a composition containing AMIDEK TM protease (Genencor International, Rochester, N.Y.) (300 μl of 20 mg/ml solution) for a few seconds at room temperature prior to adding the antigen to the test wells of the test devices. Dye-providing composition B was used in this example, and the concentration of antibody reagent was reduced 25% from that of Example 1. The coverage of antibody on the polymeric particles was 1.5 times that used in Example 1.

The wash composition comprised TERGITOL TM 4 anionic surfactant (1.35%), casein (0.5%) and thimerosal (0.1%) in glycine buffer (0.1 molar, pH 10). The Control assay used a wash composition comprising sodium decyl sulfate (1.8%) in phosphate buffer (0.1 molar, pH 7.3).

Antigen was extracted from P.g. serotypes A, B and C, P.i. serotype A and A.a. serotype B. Antigen concentrations tested were $1.25 \times 10^8$ cells/ml, $1.56 \times 10^7$ cells/ml and $1.95 \times 10^6$ cells/ml for P.g. and P.i. and The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

We claim:

1. An aqueous wash composition for specific binding assays buffered to a pH of less than or equal to about 6 or greater than or equal to about 9, said composition comprising:

at least about 0.1 weight percent of an anionic surfactant which is represented by the formula:

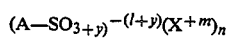

$$(A-SO_{3+y})^{-(l+y)}(X^{+m})_n$$

wherein A is an alkyl or alkyl-substituted phenyl having a molecular weight of from about 180 to about 250, $X^{+m}$ is hydrogen or a monovalent or divalent cation, m is 1 or 2, y is 0 or 1, and n is 1 or 2 provided that m and n are not both 2.

2. The composition of claim 1 buffered to a pH of from about 9.5 to about 11.

3. The composition of claim 1 comprising from about 1 to about 5 weight percent of said surfactant.

4. The composition of claim 1 further comprising a nonimmunoreactive protein.

5. The composition of claim 4 wherein said nonimmunoreactive protein is selected from the group consisting of: casein or another milk proteins, serum proteins and fibrinogen.

6. The composition of claim 1 wherein A is alkyl having from 14 to 16 carbon atoms, m and y are both 1, and n is 2.

7. The composition of claim 6 wherein A is tetradecyl, and $X^{+m}$ is a sodium or potassium ion.

8. An aqueous wash composition for immunoassays buffered to a pH of from about 9.5 to about 11, said composition comprising:

from about 1 to about 5 weight percent of an anionic surfactant which is represented by the formula:

$$(A\text{---}SO_{3+y})^{-(l+Y)}(X^{+m})_n$$

wherein A is tetradecyl, $X^{+m}$ is a sodium or potassium ion, m and y are both 1, and n is 2.

* * * * *